United States Patent
Liu et al.

(10) Patent No.: US 6,475,520 B1
(45) Date of Patent: Nov. 5, 2002

(54) PHARMACEUTICAL COMPOSITION WITH LOW TOXICITY FOR ANTI-INFLAMMATION AND ANTI-EXUDATION

(75) Inventors: Wanhui Liu, Shandong (CN); Qingchun Zhang, Shandong (CN); Shixu Li, Shandong (CN); Kajia Su, Shandong (CN); Shuyan Liu, Shandong (CN); Fabing Zhu, Shandong (CN)

(73) Assignee: Shandong Luye Pharmaceutical Co., Ltd., Shandong (CN)

( * ) Notice: Subject to any disclaimer, the term of this patent is extended or adjusted under 35 U.S.C. 154(b) by 0 days.

(21) Appl. No.: 09/787,338

(22) PCT Filed: Dec. 30, 1999

(86) PCT No.: PCT/CN99/00222

§ 371 (c)(1), (2), (4) Date: Mar. 16, 2001

(87) PCT Pub. No.: WO01/49293

PCT Pub. Date: Jul. 12, 2001

(51) Int. Cl.$^7$ .................................................. A61K 9/20
(52) U.S. Cl. ........................ 424/464; 424/451; 514/23; 514/24; 514/25; 514/54
(58) Field of Search .................................. 424/451, 464; 514/23, 24, 25, 54

(56) References Cited

FOREIGN PATENT DOCUMENTS

| JP | 10017591 | | 1/1998 |
|---|---|---|---|
| JP | 10-017591 | * | 1/1998 |

OTHER PUBLICATIONS

Matsuda et al. Bio L. Pharm. Bull. 1997, 20(10), 1092–1095.*
Matsuda et al. 1997, 7(13), 1611–1616.*
Biol. Pharm. Bull. (1997), 20 (10), 1092–1095.
Bioorg. Med. Chem. Lett (1997), 7 (13), 1611–1616.
J. Smooth, Muscle. Res. (1996), 32 (5), 219–228.
Chem. Pharm. Bull. (1998), 46 (11), 1764–1769.

* cited by examiner

Primary Examiner—Thurman K. Page
Assistant Examiner—Lakshmi Channavajjala
(74) Attorney, Agent, or Firm—Burns, Doane, Swecker & Mathis, L.L.P.

(57) ABSTRACT

The present invention relates to a pharmaceutical composition with low toxicity for anti-inflammatory and anti-exudative which contains as active ingredients escin with general formula I and escin with general formula II as well as pharmaceutically acceptable carrier or excipient. In comparison with ESCIN, this pharmaceutical composition possesses the same anti-inflammatory and anti-exudative activity, but both toxicity and irritation lower remarkably.

5 Claims, No Drawings

PHARMACEUTICAL COMPOSITION WITH LOW TOXICITY FOR ANTI-INFLAMMATION AND ANTI-EXUDATION

FIELD OF THE INVENTION

The present invention relates to the pharmaceutical composition with low toxicity for anti-inflammation and anti-exudation. Particularly, this pharmaceutical compositon contains as active components escin compounds of general formula I and general formula II obtained from the ESCIN as well as a pharmaceutical carrier and excipient.

BACKGROUND

The ESCIN is an active component for anti-inflammation and anti-exudation, which is obtained by extraction from dry and ripen seed of the plant of Aesculus (buckeye). Recently the injection of ESCIN is wildly applied in clinic for the treatment of cerebral edema complicating dysfunction of brain, burn, scald, chronic incompetence of vein, wound, fracture, edema and hematoma after the operation. Even so, because of higher toxicity and side effects of ESCIN ($LD_{50}$ is 3.99 mg/kg only) with its stronger stimulation after administrating, this drug is restricted during the clinical use. The Japanese Laid Open Hei 10-17591 disclosed some anti-inflammatory agents containing the compounds of formula IA, IB or the mixture of them.

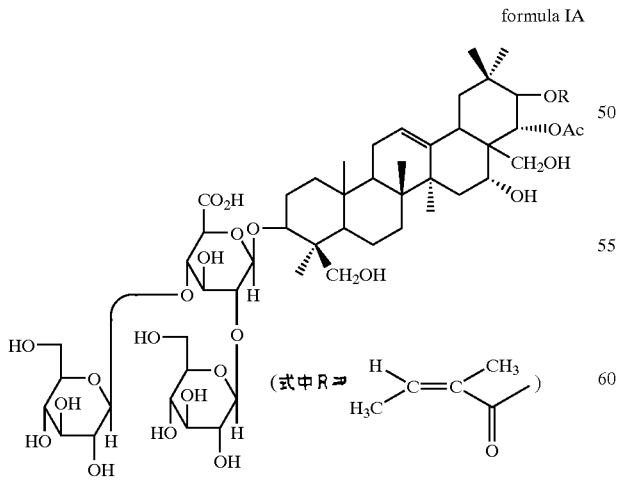

formula IA

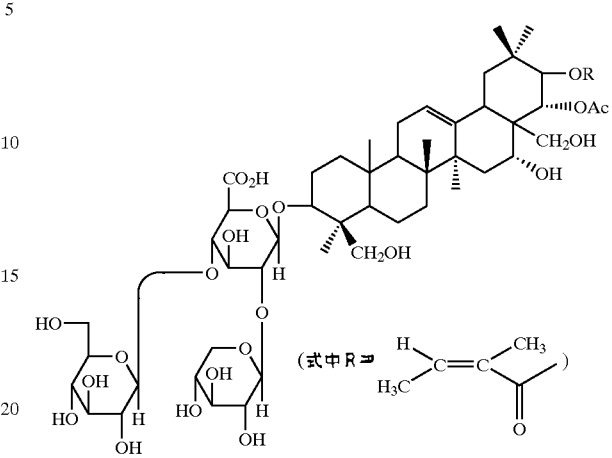

formula IB

Therefore, it is still necessary to develop some pharmaceutical compositions with low toxicity and low side effects for anti-inflammation and anti-exudation.

OBJECT OF THE INVENTION

The object of the present invention is searching for and developing some pharmaceutical compositions with low toxicity and low side effects for anti-inflammation and anti-exudation.

SUMMARY OF THE INVENTION

The inventors have made wide and deep study and discovered that the compositions containing escin having the general formula I and II maintain the ESCIN having activity of anti-inflammation and anti-exudation by the ESCIN, and the toxic action and side effects are lowered simultaneously. The present invention is accomplished thereby. Consequently the present invention relates to a new pharmaceutical composition including escin compounds with formula I and II as well as a pharmaceutical carrier or excipient. Such composition retaining the activity of ESCIN simultaneously can greatly lower the toxicity and side effect of ESCIN.

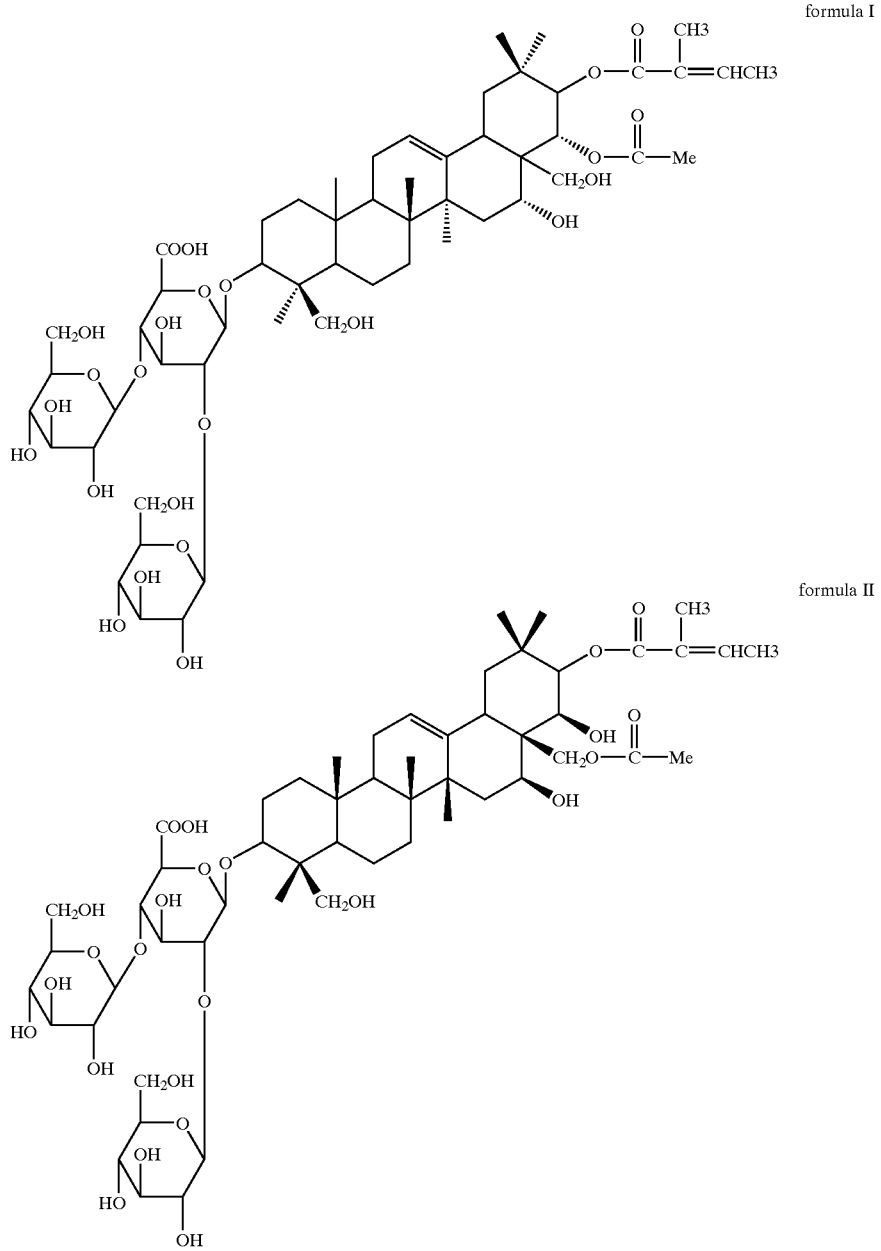

formula I formula II

According to the present invention, the term "escin with general formula I" used in the present application refers to such a stereoisomer which is consisted of 21-position (Z) (cis-form) and (E) (trans-form) of general formula I.

According to the present invention, the term "escin with general formula II" used in the present application refers to such a stereoisomer which is consisted of 21-position (Z) (cis-form) and (E) (trans-form) of general formula II.

DETAILED DESCRIPTION OF THE INVENTION

The present invention relates to a new pharmaceutical composition with low toxicity and side effects for anti-inflammation and anti-exudation. This pharmaceutical composition contains as active components escin compounds of general formula I and general formula II as well as a pharmaceutical carrier and excipient.

According to the present invention, the weight ratio of escin with general formula II and escin with general formula I in the said pharmaceutical composition is 1–7:3–9, preferable 2.5–4.5:5.5–7.5 and the most preferably 4:6.

According to the present invention, as to for the activity of anti-inflammation and anti-exudation, the pharmaceutical composition of the present invention has the same order of magnitude as compared to the known pharmaceutical preparation of ESCIN, but the toxic and side effects, such as acute toxicity, are significantly lower than those of the known preparation of ESCIN. For example, the $LD_{50}$ of ESCIN is 3.99 mg/kg, while that of pharmaceutical composition of the present invention is 5.99 mg/kg. The more detailed illustration dealing with the activity of anti-inflammation and anti-exudation as well as the low toxicity will be observed in the following experimental examples.

According to the present invention, escin with general formula I and II can be obtained by extraction from the dried ripe fruit of *Aesculus chinensis* according to the known methods in this field. A similar method has been published in << Zhong Cao Yao>> (Chinese Herbal Medicine), Vol. 5, 327–331, 1999. Their preparative method in detail will be seen in the following Example 1.

According to the present invention, the pharmaceutical composition of the present invention may contain a variety of pharmaceutically acceptable carriers or excipients. These pharmaceutical carriers and excipients include filling material, binding agent, wetting agent, disintegrant, surface active agent, lubricant, diluent etc. The addition of the pharmaceutical carrier or excipient depends on the dosage form of pharmaceutical composition of the present invention. For example, if the pharmaceutical composition of the present invention is in the form of tablet, the conventional pharmaceutical carrier or excipient used for preparing tablets may be included, such as wetting agent, lubricant and filling material. If the pharmaceutical composition of the present invention is in the form of liquid, diluents, such as distilled water and glucose liquor etc. may be included. The selected pharmaceutical carriers and excipients would not react with the active components in the pharmaceutical composition of the present invention. There is no any limitation besides these.

In virtue of lowering toxicity and increasing safety, the conventional pharmaceutical technology has been adopted for preparing a variety of dosage forms of the pharmaceutical composition of the present invention, such as the preparation for administration by gastrointestinal tract and those by non-gastrointestinal tract. Among them, the preparations for gastrointestinal tract include oral liquor, tablet, syrup, capsule, granule etc. while that for non-gastrointestinal tract includes injection as well as the preparations for topical use, such as eye drops, suppository, vaginal suppository, gel and spray agent.

Furthermore, the present invention will be illustrated in detail by the following examples, but it does not mean that the present invention is only limited to these examples.

Preparation of escin with general formula I and II

EXAMPLE 1

Weighing 1.0 kg of the powder of dried ripe fruit of *Aesculus chinensis*, 5 L of 25% ethanol are added and the obtained mixture is soaked overnight, extracted twice with stirring for each 6 hrs. the extraction is combined and the drug residue is filtered off. The extraction is treated by passing through 1.0 kg of D-101 adsorbent macroporous resin. The resin is eluted with distilled water to colorless and the impurity is washed off with 5 L of 25% ethanol. Finally it is eluted with 5 L of 95% ethanol and the ethanolic extract of ESCIN is obtained. The final extract is concentrated to a volumn of 500 ml. After adding 5 L of acetone into 500 ml concentrate, the white precipitate is formed. The latter is filtered out and dried under vacuum at 60° C. 15.0 g ca. of ESCIN is obtained and dissolved in 500 ml of distilled water under heating, filtering, the obtained filtrate is placed in a refrigerator at 4° C. for 30 min. The white crystal is collected, washed with distilled water. After drying under vacuum at 60° C. escin with general formula I is thus obtained. The remaining water solution is treated with 50 g of D-101 adsorbent macroporous resin and eluted with 500 ml of 95% ethanol. The ethanolic solution of escin with general formula II is obtained, concentrated to 50 ml and concentrate liquid is placed in a refrigerator at 4° C. The white flake crystal is collected by filtration, washed with distilled water and dried at 60° C. The escin with general formula II is thus obtained.

The physical and chemical characteristics of escin with general formula I are as follows:

m.p.:253–256° C., $M^+$(FAB-MS):1153 ($MM^++Na$), $IRcm^{-1}$:1649, 1653, 1708, 1731, 3404; $^1HNMR[\delta]$:1.61, 1.87, 1.92. $^{13}CNMR[\delta]$:129.1, 136.8, 167.8, 170.8.

The physical and chemical characteristics of escin with general formula II, a white powder, are as follows:

$M^+$(FAB-MS):1153 ($M^++Na$), $IRcm^{-1}$:1074, 1640, 1713, 1740, 3409; $^1HNMR[\delta]$:1.56, 1.92. $^{13}CNMR[\delta]$:129.5, 136.8, 168.5, 170.7.

EXAMPLE 2

| Freeze-dried powder for injection | |
|---|---|
| Escin with general formula I | 7 mg |
| Escin with general formula II | 3 mg |
| Water for injection | q.s. |

Escin with general formula I and II are dissolved in water for injection to prepare the freeze-dried powder for injection according to the said conventional method for injection.

EXAMPLE 3

| Injection | |
|---|---|
| Escin with general formula I | 1 mg |
| Escin with general formula II | 9 mg |
| 0.9% normal saline | to 1000 ml |

Escin with general formula I and II are dissolved in normal saline and the injection is prepared by the conventional process for preparing injection.

EXAMPLE 4

| Tablet | |
|---|---|
| Escin with general formula I | 4 mg |
| Escin with general formula II | 6 mg |
| Starch | 20 mg |
| Magnesium stearate | 5 mg |

The tablet is prepared by the conventional process for preparing tablet.

EXAMPLE 5

| Eye drops | |
|---|---|
| Escin with general formula I | 6 mg |
| Escin with general formula II | 4 mg |
| 0.9% normal saline | 1000 ml |

The eye drops is formulated by means of the above-mentioned components.

EXAMPLE 6

| Gel agent | |
|---|---|
| Escin with general formula I | 4.5 mg |
| Escin with general formula II | 5.5 mg |

The above-mentioned components are used as active ingredients. The ordinary excipient used for preparing gel agent is added into the above active ingredients and the gel agent is prepared by the conventional process for preparing gel agent.

EXAMPLE 7

| Spray agent | |
|---|---|
| Escin with general formula I | 2.5 mg |
| Escin with general formula II | 7.5 mg |

The above-mentioned components are used as active ingredients. The ordinary excipient used for preparing spray agent is added into the above ingredients and the spray agent is prepared by the conventional process for preparing spray agent.

TEST EXAMPLE 1

Anti-inflammation Test

Test sample: General escin (white powder) with the purity 96.3%,
Escin with general formula I with the purity 98%,
Escin with general formula II with the purity 97%, in which
Escin with general formula II: Escin with general formula I=4:6 (weight ratio).
All the above-mentioned samples are treated by sterilization and pyrogen elimination.
The injection is formulated with 0.9% normal saline before use. Test animal: healthy mice (Kunming) with weight of 25–30 g, male and female in half and half.

Route of administration: Intra-peritoneal.
Dose: 0.7 mg/kg
Test method: 10 mice per group for the test. General escin, escin with general formula I and II are given intra-peritoneally to the test animals. After 30 min, 30 µl of xylene are dropped into the auris dexter of every mouse on both positive and negative side and after 30 min the mice are put to death successively. The binaural disks of mice are taken down with a 7.0 mm borer and weighed. The degree of swelling is evaluated (the weight of auris dextra minus that of auris sinistra). Results are shown in the following table:

| Group | Control | General escin | Escin with general formula I + Escin with general formula II |
|---|---|---|---|
| Number of animal | 10 | 10 | 10 |
| Degree of swelling | 12.31 ± 1.24 | 8.33 ± 2.82*** | 8.73 ± 2.64** |
| Rate of inhibition of swelling | — | 32.33 | 29.08 |

In comparison with the control, $P < 0.01$, *$P < 0.001$

Thus it can be seen that the anti-inflammatory action of the active ingredients contained in the pharmaceutical composition of the present invention is basically in the same level as that of ESCIN. The difference has no statistical significance with each other.

TEST EXAMPLE 2

Anti-exudation Test

Test sample:

General escin (white powder) with the purity 96.3%,
Escin with general formula I with the purity 98%,
Escin with general formula II with the purity 97%, in which Escin with general formula II: Escin with general formula I=4:6 (weight ratio).
All the above-mentioned samples are treated by sterilization and pyrogen elimination.
The injection is prepared with 0.9% normal saline before use.
Test animal: healthy mice (Kunming) with weight of 18–24 g, male and female in half and half.
Route of administration: Subcutaneous injection
Dose: 1.4 mg/kg
Test method: The test samples or normal saline listed in the following table are given by subcutaneous injection. After 40 min 0.1 mg/kg of 0.55 Evans stain is given intravenously and 0.3 ml 0.2% HAc is injected intra-peritoneally for each animal at random. After 20 min the mice are put to death successively. The abdominal cavity is cut with a scissors and washed with normal saline. The wash water is sucked out to a 10 ml- centrifuge tube and centrifugalized at 3000 rpm for 15 min. The absorbance of the supernatant liquid is determined at 590 nm. The comparison is made among groups.

Results are shown in the following table:

| Group | Control | General escin | Escin with general formula I + Escin with general formula II (4:6 w/w) |
|---|---|---|---|
| Number of animal | 10 | 9 | 10 |
| Degree of swelling | $0.480 \pm 0.038$ | $0.287 \pm 0.126$*** | $0.338 \pm 0.058$*** |
| Rate of inhibition of swelling | — | 40.2 | 29.6 |

In comparison with the control, P < 0.01, *P < 0.001

Thus it can be seen that the anti-exudative action of the active ingredients contained in the pharmaceutical composition of the present invention is basically in the same level as that of ESCIN. The difference has no statistical significance with each other.

TEST EXAMPLE 3

Acute Toxicity Test

Test animal: healthy mice (Kunming) with weight of 19–21 g, male and female in half and half.

Test sample:

General escin (white powder) with the purity 96.3%,

Escin with general formula I with the purity 98%,

Escin with general formula II with the purity 97%, among which

Escin with general formula II: Escin with general formula I=4:6 (weight ratio).

All the above-mentioned samples are treated by sterilization and pyrogen elimination.

The injection is prepared with 0.9% normal saline before use.

Test dosage: Six dosage groups are selected and the interval of the groups depends upon the results of preliminary test.

Route of administration: Intravenous

Test method: Animals are devided into six groups at random according to the body weight of a animal. Every group has 10 mice in which male and female in half and half. After administration the reaction of animal is observed and the distribution recorded within 7 days.

The results show as follows:

1. $LD_{50}$ of escin with general formula I + escin with general formula II

| No. of animal | Body weight(g) | Dose (mg/kg) | No. of death | Death rate % |
|---|---|---|---|---|
| 10 | $19.7 \pm 1.3$ | 15.00 | 10 | 100 |
| 10 | $19.5 \pm 1.6$ | 11.70 | 10 | 100 |
| 10 | $19.6 \pm 2.0$ | 9.12 | 8 | 80 |
| 10 | $19.2 \pm 1.8$ | 7.12 | 6 | 60 |
| 10 | $19.4 \pm 1.8$ | 5.55 | 5 | 50 |
| 10 | $19.6 \pm 1.9$ | 4.33 | 2 | 20 |

(1:K = 1:0.78)

| $LD_5$ | $LD_{50}$ | $LD_{95}$ | Regression equation |
|---|---|---|---|
| 3.12 | 5.99 | 11.51 | $E = 0.487 + 5.803 \log(D)$ |
| 1.80 – 4.54 | 4.56 – 7.08 | 8.51 – 17.80 | |

2. $LD_{50}$ of General escin

| No. of animal | Body weight(g) | Dose (mg/kg) | No. of death | Death rate % |
|---|---|---|---|---|
| 10 | $19.8 \pm 1.8$ | 15.00 | 10 | 100 |
| 10 | $19.7 \pm 1.6$ | 10.50 | 10 | 100 |
| 10 | $19.6 \pm 1.8$ | 7.35 | 9 | 90 |
| 10 | $19.7 \pm 1.4$ | 5.14 | 5 | 50 |
| 10 | $19.1 \pm 1.7$ | 3.60 | 4 | 40 |
| 10 | $19.3 \pm 1.5$ | 2.52 | 3 | 30 |

(1:K = 1:0.75)

| $LD_5$ | $LD_{50}$ | $LD_{95}$ | Regression equation |
|---|---|---|---|
| 1.57 | 3.99 | 10.13 | $E = 2.56 + 4.061 \log(D)$ |
| 0.54 – 2.47 | 2.91 – 5.06 | 7.03 – 23.20 | |

3. $LD_{50}$ of escin with general formula I

| No. of animal | Body weight(g) | Dose (mg/kg) | No. of death | Death rate % |
|---|---|---|---|---|
| 10 | $18.8 \pm 1.0$ | 7.00 | 8 | 80 |
| 10 | $19.0 \pm 0.7$ | 5.25 | 8 | 80 |
| 10 | $19.0 \pm 0.9$ | 3.94 | 5 | 50 |
| 10 | $19.2 \pm 0.4$ | 2.95 | 2 | 20 |
| 10 | $19.0 \pm 0.0$ | 2.21 | 1 | 10 |
| 10 | $19.2 \pm 0.4$ | 1.66 | 0 | 0 |

(1:K = 1:0.75)

| $LD_5$ | $LD_{50}$ | $LD_{95}$ | Regression equation |
|---|---|---|---|
| 1.96 | 4.12 | 8.65 | $E = 1.86 + 5.11 \log(D)$ |
| 1.21 – 3.18 | 3.20 – 5.30 | 4.96 – 15.10 | |

Result:

The $LD_{50}$ value of the active ingredients in the pharmaceutical composition of the present invention is compared with the $LD_{50}$ value of ESCIN ingredients intravenous injection. The result is as follows:

| Classification of the compounds | $LD_{50}$ value (mg/kg) |
|---|---|
| General escin | 3.99 |
| Escin with general formula I + II | 5.99 |
| Escin with general formula I | 4.12 |

Thus it can be seen that the $LD_{50}$ value of active ingredients in the pharmaceutical composition of the present invention is obviously higher than that of ESCIN. It is also said that the toxicity of the active ingredients in the pharmaceutical composition of the present invention is obviously low.

What is claimed is:

1. A pharmaceutical composition with low toxicity for anti-inflammatory and anti-exudative which contains as active components escin with general formula I and escin with general formula II as well as pharmaceutically acceptable carrier or excipient.

General formula I

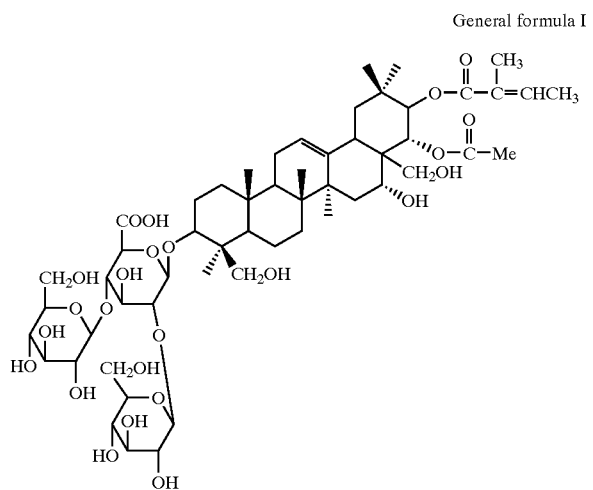

General formula II

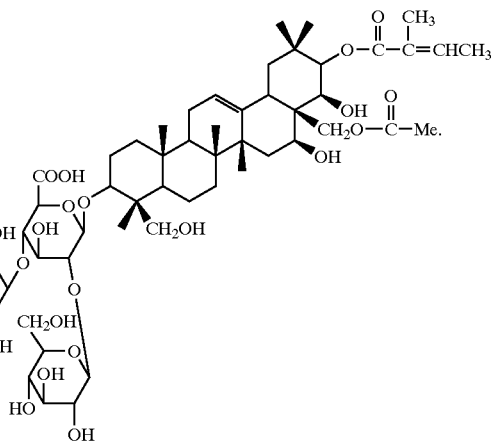

2. A pharmaceutical composition according to claim 1, in which the weight ratio of escin with the general formula II an escin with general formula I is 1–7:3–9.

3. A pharmaceutical composition according to claim 2, in which the. weight ratio of escin with general formula II and escin with general formula I is 2.5–4.5:5.5–7.5.

4. A pharmaceutical composition according to claim 3, in which the weight ratio of escin with general formula II and escin with general formula I is 4:6.

5. A pharmaceutical composition in claim 1, their dosage forms are tablet, capsule, freeze-dried powder for injection, gel agent, suppository and spray.

* * * * *